United States Patent [19]
Kaul et al.

[11] Patent Number: 4,775,993
[45] Date of Patent: Oct. 4, 1988

[54] X-RAY DIAGNOSTICS INSTALLATION

[75] Inventors: Karlheinz Kaul, Uttenreuth; Eckard Seuss, Baiersdorf, both of Fed. Rep. of Germany

[73] Assignee: Siemens Aktiengesellschaft, Berlin & Munich, Fed. Rep. of Germany

[21] Appl. No.: 37,791

[22] Filed: Apr. 13, 1987

[30] Foreign Application Priority Data

May 7, 1986 [DE] Fed. Rep. of Germany ....... 3615481

[51] Int. Cl.$^4$ ............................................. H05G 1/54
[52] U.S. Cl. ...................................... 378/117; 378/91; 378/114; 378/96
[58] Field of Search .................. 378/91, 96, 114, 115, 378/117

[56] References Cited

U.S. PATENT DOCUMENTS

| | | | |
|---|---|---|---|
| 2,883,546 | 4/1959 | Leishman | 378/91 |
| 3,025,401 | 3/1962 | Lauterbach | 378/98 |
| 3,302,022 | 1/1967 | Brenner et al. | 378/91 |
| 3,986,033 | 10/1976 | Mester et al. | 378/96 |
| 4,293,927 | 10/1981 | Hoshii | 369/900 |

FOREIGN PATENT DOCUMENTS 2341975 10/1974 Fed. Rep. of Germany .
2255038 7/1975 France .

OTHER PUBLICATIONS

Siemens sale brochure *Multigraph*, Order No. A191-00-M1026-A629-01-7600, 1984.
Siemens sales brochure, *Multigraph*, Order No. A910-01-M1026-G232-01, 1985.

*Primary Examiner*—Craig E. Church
*Assistant Examiner*—John C. Freeman
*Attorney, Agent, or Firm*—Hill, Van Santen, Steadman & Simpson

[57] ABSTRACT

The present invention is directed to an X-ray diagnostics installation having control elements for control of specific components of the installation. In order to prevent inadvertent actuation of the elements, an activation switch must be actuated to cause each of the control elements to be effective for a predetermined time. The length of the predetermined time can be increased by actuation of one of the control elements following the actuation of the activation switch.

3 Claims, 2 Drawing Sheets

X-RAY DIAGNOSTICS INSTALLATION

BACKGROUND OF THE INVENTION

The present invention is directed to an X-ray diagnostics installation comprising control elements for controlling defined components and comprising an activation switch by means of which the control elements can be switched from an ineffective condition to an effective condition.

An X-ray diagnostics installation of a C-bend or C-frame has an X-ray radiator and an X-ray receiver at its ends to form an X-ray system. An apparatus of this type can be employed for angiocardiography. The region of the patient to be examined is therefor selected by adjusting the C-frame along its circumferential direction, by swiveling the frame and by displacing the column on which the frame is mounted. These movements can be remotely controlled at a control box at which control elements for this purpose are provided and these are particularly capable of being fashioned as rocker levers or switches.

SUMMARY OF THE INVENTION

The object of the present invention is to provide an X-ray diagnostics installation having control elements for controlling defined components wherein no control event is triggered given inadvertent actuation of a control element, particularly a rocker lever. In particular, no apparatus adjustment can occur when one of the corresponding control elements is inadvertently actuated, for example when brushed by clothing or with the arm.

To achieve these objects, the present invention is directed to improvement in an X-ray diagnostics installation having control elements for the control of specific components and having an actuation switch by means of which the control elements can be switched activatably in effective in common. The improvement is that a timer is actuated by an actuation of the actuation switch and this timer switched the control elements to an effective condition for a predetermined time.

Thus, the object is achieved in accordance with the present invention by the timer element which activates the control elements during a predetermined time after the actuation of the actuation switch has occurred.

In the X-ray diagnostics installation of the invention, the user must intentionally actuate the actuation switch before triggering a control event. The actuation switch thereby activates the control elements, preferably during a predetermined time so that they only trigger control events only in this time period. Unintentional control of events are practically eliminated.

An especially expedient embodiment occurs when the activation switch is attached to the control box together with the control elements. This control box is arranged at the patient supporting table.

Further objects and advantages will be readily apparent from the following description of the preferred embodiments, the drawings and the claims.

DESCRIPTION OF THE PREFERRED EMBODIMENTS

Figure 1:
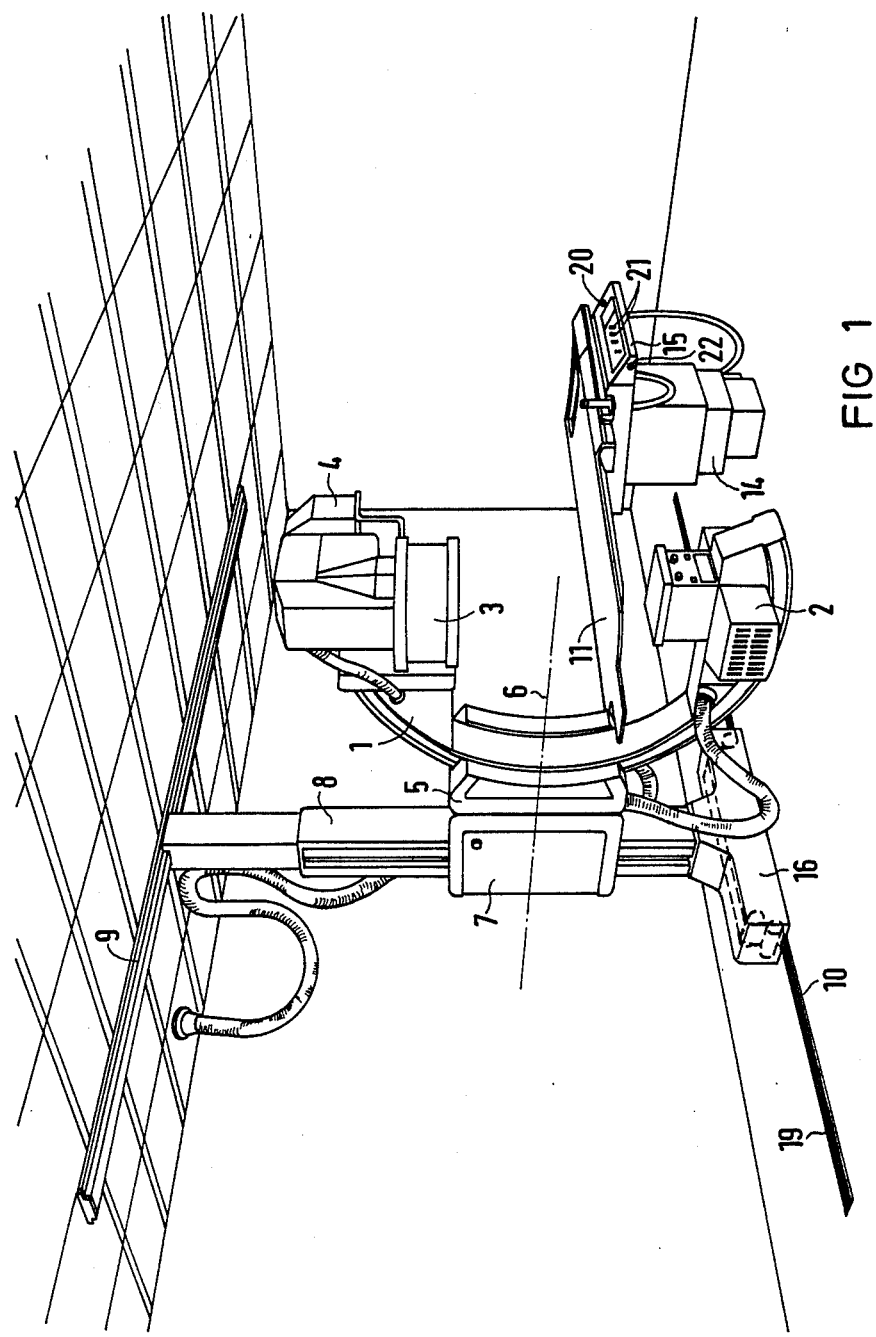
FIG. 1 is a perspective view of an X-ray diagnostics installation in accordance with the present invention.

The principals of the present invention are particularly useful in an X-ray diagnostics device having a C-frame 1, which carries an x-radiator 2 and an X-ray image intensifier 3 with a following single-frame camera 4 as well as a video camera (not visible) at the ends of the frame. The C-frame 1 is mounted in a holder 5 and is displaceable along its circumference. The holder 5 is mounted on a truck 7 for pivotal movement around a horizontal axis 6. The truck 7 is mounted for longitudinal displacement on a vertical column 8. The column 8 is displaceable on a ceiling rail 9 and a floor rail 10 which extend parallel to one another and to the longitudinal direction of a patient support table 11. The C-frame 1 transversely embraces the patient support table 11. The table 11 is positioned on a pedestal 14 in a height-adjustable fashion. A control panel 15 is secured to this pedestal 14 and is displaceable in a longitudinal and transverse direction relative to the pedestal 14 by floating bearings; however, the adjustment path in the longitudinal direction is relatively small and in the order of magnitude of 40 cm.

The selection of the area examined essentially occurs by setting the x-radiator 2 and the X-ray image intensifier 3 without adjusting the patient support table 11. The adjustment can therefore occur in the following way:

First, the column 8 is displaced entirely toward the left (FIG. 1) by the motor drive. In this position thus reached, the C-frame 1 is brought into a respective examination position with the image intensifier 3 above or below the patient support table 11 or laterally positioned therefrom. Subsequently, the column 8 is moved back to the right until the x-radiator 2 and the X-ray image intensifier 3 lie at the particular area of the patient to be irradiated. It should be noted, the x-radiator may lie under the patient or above the patient or be laterally positioned relative thereto. The respective height of the isocenter is thereby set via the truck 7. Finally, the emission direction can also be further varied by swiveling the C-frame 1 around the axis 6.

At its underside, the column 8 is connected to a truck 16 which has wheels guided in the rail 10. The rail 10 is formed by an upwardly open, slotted hollow profile in which the wheels run. The open upper side of the rail 10 is covered by a flexible band 19 which proceeds through the truck 16 and consequently prevents articles from falling into the inside of the slotted hollow profile of the rail 10.

The control of the individual components of the X-ray diagnostics installation of FIG. 1 occur by control elements on a control box 20 which is attached to the patient support table 11. The control box 20 particularly carries rocker levers 21 which control the various electromotive movements of the individual components of the X-ray diagnostics installation. The rocker elements 21 can be inadvertently actuated by a person passing the control box 20. So that no control events are accidentally initiated, an activation key 22 is present at the left-hand end face of the control box 20. When the activation key 22 is actuated, then the rocker levers 21 are activated during a predetermined time, for example 20 seconds. This means that the control event can be initiated with the assistance of the rocker levers 21 only during this time after the actuation of the actuation key 22. When the time of 20 seconds after the actuation of the activation key 22 has elapsed, then the actuation of the rocker levers 21 remains ineffective.

Figure 2:
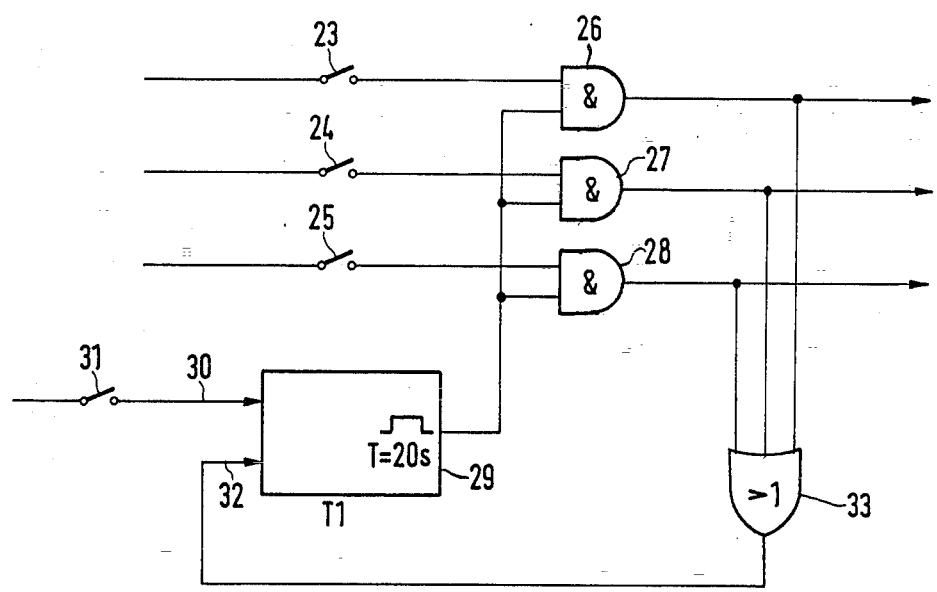
FIG. 2 is a circuit diagram of the parts of the x-ray diagnostics installation of FIG. 1 essential for the special control features of the invention.

A control circuit is illustrated in FIG. 2. In this circuit, contacts 23, 24 and 25 are actuated by three of the rocker levers 21. The contacts 23 through 25 are connected to three AND gates 26, 27 and 28, respectively, whose second input comes from a timer 29. The timer 29 has an input 30 which leads to a switch 31 which can be actuated by the activation key 22. A second input 32 for the timer 29 is connected to an output of an OR gate 33 which receives outputs from each of the AND gates 26, 27 and 28, which outputs are leading to the control electronics.

When the activation key 22 is actuated and, thus, the switch 31 is closed, the timer 29 is triggered and the switches 23, 24 and 25 are in an effective condition for apparatus control during a time of 20 seconds. When one of the switches 23, 24 and 25 is actuated during this time interval, then an output pulse is generated at the corresponding AND gate 26, 27 and 28, respectively. This output from one of the AND gates 26, 27 and 28, in addition to driving the associated electronics, will also be applied to the OR gate 33 to create a reset pulse to continually reset the timer 29 so that another 20 seconds will occur. Thus, if, after the closing of the activation key, which closes the switch 31, one of the switches 23, 24 and 25 is closed, during the 20 second time period, then the actuation will continue over a period for more than 20 seconds as long as the switch is held closed. However, if after the activation key 22 is closed to close the switch 31, none of the switches 23, 24 and 25 is actuated during the 20 second period, then a subsequent actuation of one of these switches would not produce an output because the pulse would be over and the output from the timer 29 would have stopped.

It should also be noted that instead of using the above-mentioned logic circuit, the same function could be realized utilizing a software program.

Although various minor modifications may be suggested by those versed in the art, it should be understood that we wish to employ within the scope of the patent granted hereon, all such modifications as reasonably and properly come within the scope of our contribution to the art.

We claim:

1. In an X-ray diagnostics installation having an X-ray source and a source positioning means comprising control switches for energizing said positioning means, the improvements comprising timer means including an activation switch for enabling said control switches for a predetermined period of time, said activation switch starting said timer means.

2. In an X-ray diagnostics installation according to claim 1, including a patient support table and wherein said activation switch together with said control switches are attached to a control box which is arranged at the patient support table.

3. In an X-ray diagnostics installation according to claim 1, wherein the timer means includes means for receiving an input starting signal from each of the control switches so that if the control switches are actuated during the predetermined time after the timer means has been actuated, the timer means is reset to enable extending the time period.

* * * * *